US012653912B2

(12) United States Patent
Liu et al.

(10) Patent No.: US 12,653,912 B2
(45) Date of Patent: Jun. 16, 2026

(54) APPLICATION OF MITOXANTRONE PREPARATION IN PREPARATION OF DRUG FOR DIAGNOSING AND TREATING DISEASE RELATED TO THYROIDECTOMY

(71) Applicants: SHENZHEN CHINA RESOURCES JIUCHUANG MEDICAL AND PHARMACEUTICAL CO., LTD, Shenzhen (CN); SHENZHEN CHINA RESOURCES GOSUN PHARMACEUTICALS CO., LTD, Shenzhen (CN)

(72) Inventors: Jun Liu, Shenyang (CN); Xun Li, Shenyang (CN); Zhanao Yang, Shenzhen (CN); Feina Tu, Shenzhen (CN); Ning Chen, Shenzhen (CN); Quanhua Huang, Shenzhen (CN); Huacheng Liang, Shenzhen (CN); Baolin Lai, Shenzhen (CN); Weiwei Zhang, Shenzhen (CN)

( * ) Notice: Subject to any disclaimer, the term of this patent is extended or adjusted under 35 U.S.C. 154(b) by 663 days.

(21) Appl. No.: 17/999,969

(22) PCT Filed: Mar. 23, 2021

(86) PCT No.: PCT/CN2021/082261
§ 371 (c)(1),
(2) Date: Nov. 28, 2022

(87) PCT Pub. No.: WO2021/238367
PCT Pub. Date: Dec. 2, 2021

(65) Prior Publication Data
US 2023/0201378 A1 Jun. 29, 2023

(30) Foreign Application Priority Data
May 27, 2020 (CN) .......................... 202010464323.1

(51) Int. Cl.
*A61K 49/00* (2006.01)
(52) U.S. Cl.
CPC ................................. *A61K 49/006* (2013.01)
(58) Field of Classification Search
None
See application file for complete search history.

(56) References Cited

FOREIGN PATENT DOCUMENTS

| | | |
|---|---|---|
| CN | 102397561 | 4/2012 |
| EP | 0028917 | 5/1981 |
| WO | 2010030120 | 3/2010 |

OTHER PUBLICATIONS

Chen et al Poster 14—Mitoxantrone Hydrochloride is a Novel Lymphatic Tracer That May Help Preserving Parathyroid Glands in Thyroid Surgery. 87th Annual Meeting of the American Thyroid Association. vol. 27, S1, 2017). (Year: 2017).*
Wang et al.(CN102397561; wherein a machine translation is provided). (Year: 2013).*
Ma, Yukui et al., "Non-official translation: Sub-chronic Toxicity of Mitoxantrone Hydrochloride for Subcutaneous Injection of Lymphatic Tracing in Rats", Chinese Journal of Pharmacology and Toxicology,vol. 27, No. 3, Jun. 30, 2013 (Jun. 30, 2013).
Celikoglu, F. et al., "Intratumoural Chemotherapy of Lung Cancer for Diagnosis and Treatment of Draining Lymph Node Metastasis.", Journal of Pharmacy and Pharmacology.,vol. 62, Dec. 31, 2010 (Dec. 31, 2010), pp. 287-295.
Kiong, Subin et al., "RP-HPLC Study on the Tissue Distribution and Lymph Node Targeting of Mitoxantrone Loaded Albumin Nanoparticles RP-HPLC Method for Determination of Mitoxantrone in Rat Plasma and Different Tissues", (Chinese Journal of Pharmaceutical Analysis),vol. 26, No. 8, Dec. 31, 2006 (Dec. 31, 2006), pp. 1043-1049.

\* cited by examiner

*Primary Examiner* — Jake M Vu
(74) *Attorney, Agent, or Firm* — JMB Davis Ben-David

(57) ABSTRACT

An application of a mitoxantrone preparation in preparation of a drug for diagnosing and treating a disease related to thyroidectomy, and use of mitoxantrone and/or a pharmaceutically acceptable salt thereof in preparation of a lymph tracer for preventing parathyroid gland staining in error, preventing parathyroid gland cutting in error, or reducing the rate of parathyroid gland cutting in error. Local injection of a mitoxantrone hydrochloride injection fluid would not cause parathyroid gland staining in error, and can reduce the rate of parathyroid gland cutting in error, thus protecting parathyroid glands well; moreover, no local or systemic toxic side effect is found after the local injection. The present invention has good tolerability, efficacy, and safety, and provides a new treatment idea in radically curing thyroid diseases thoroughly for patients suffering from diseases related to thyroidectomy.

15 Claims, No Drawings

APPLICATION OF MITOXANTRONE PREPARATION IN PREPARATION OF DRUG FOR DIAGNOSING AND TREATING DISEASE RELATED TO THYROIDECTOMY

CROSS-REFERENCE TO RELATED APPLICATIONS

This is the U.S. National Stage of International Patent Application No. PCT/CN2021/082261 filed on Mar. 23, 2021, which in turn claims the benefit of Chinese Patent Application No. 202010464323.1 filed on May 27, 2020.

TECHNICAL FIELD

The present disclosure belongs to the field of pharmaceutical preparations, and specifically, relates to an application of mitoxantrone for lymphatic tracing in a disease related to thyroidectomy.

BACKGROUND

Thyroid carcinoma is the most common malignant tumor developed in the endocrine system, the head, and the neck. A report from International Agency for Research on Cancer (IARC) in 2012 shows that the incidence rate of thyroid carcinoma is 4.0/100,000 and the mortality rate is 0.5/100,000 all over the world, wherein the incidence rate is 1.9/100,000 for men and 6.1/100,000 for women, with a male-to-female incidence ratio of 1:3; and the mortality rate is 0.3/100,000 for men and 0.6/100,000 for women, with a male-to-female mortality ratio of 1:2.

More than 90% of thyroid carcinoma cases are differentiated thyroid carcinoma (DTC). Treatment methods for DTC mainly include operative treatment, postoperative I treatment, and thyroid stimulating hormone (TSH) suppressive therapy. Among them, the operative treatment is most important, which directly influences subsequent treatment and follow-up of DTC and is closely associated with prognosis. Thyroidectomy for DTC mainly includes total/near total thyroidectomy and lobectomy+isthmectomy for thyroid. Total thyroidectomy refers to removal of all of the thyroid tissues, with no visible thyroid tissues remained; near total thyroidectomy refers to removal of almost all of the visible thyroid tissues (with non-neoplastic thyroid tissues of <1 g remained, such as non-neoplastic thyroid tissues at the access to the larynx of the recurrent laryngeal nerve and the parathyroid glands).

Although most patients with DTC have a good prognosis, a lower mortality rate, and a high 10-year survival rate, about 30% of patients with DTC will experience recurrence or metastasis, wherein ⅔ of the recurrence or metastasis cases occur within 10 years after operations, and patients experiencing postoperative recurrence and distant metastasis have a poor prognosis. Cervical lymph node metastasis is a risk factor for increased recurrence and decreased survival in patients with DTC (especially those aged ≥45). 20%-90% of patients with DTC have cervical lymph node metastasis at the time of diagnosis, mostly in the central area of the neck. Therefore, the "Guidelines for the Diagnosis and Treatment of Thyroid Nodules and Differentiated Thyroid Carcinoma" recommends that prophylactic central lymph node dissection should be performed in a case that the parathyroid glands and the recurrent laryngeal nerve are effectively remained in an operation for DTC.

Since central lymph node dissection easily damages the parathyroid glands, postoperative hypoparathyroidism is common. Some studies show that the incidence rate of permanent hypoparathyroidism is 2%-33% after total thyroidectomy and near total thyroidectomy, and the reason is that operations result in a high rate of parathyroid gland cutting in error, which seriously affects therapeutic effects of operations. Therefore, identifying and remaining as many parathyroid glands as possible has become an important means for preventing postoperative hypoparathyroidism. Some studies find that the lymphatic network of the thyroid and the lymphatic network of the parathyroid glands are not connected with each other, and the application of lymphatic tracers in draining the thyroid lymphatic vessels can well differentiate the thyroid from the parathyroid glands to avoid parathyroid gland cutting in error.

The existing well-known lymphatic tracing methods include: a dye method, a nuclide method, and a dye-nuclide combined tracing method.

The main dye-based lymph node tracers reported at home and abroad include methylene blue, nano-carbon, isosulfan blue, and patent blue, etc. At present, methylene blue and nano-carbon are more used as the lymph node tracers in clinic in China, while isosulfan blue and patent blue are less used in China due to their high prices and difficulty for purchasing at home.

Methylene blue, also known as methylthioninium chloride, is a water-soluble pigment dye with multiple clinical uses, which has been used as a lymph node tracer for many years, and certain clinical experiences have been accumulated during application in thyroid carcinoma. A study conducted by Jozaghi et al. on 300 cases of thyroid carcinoma in which methylene blue is used as a sentinel lymph node tracer shows that the detectable rate of lymph nodes is 68.8%, and the specificity is 100%, which proves that the application of methylene blue in intraoperative tracing and positioning of sentinel lymph nodes in the tumor can improve the intraoperative detectable rate of lymph nodes (Jozaghi Y, Richardson K, Anand S, et al. Frozen section analysis and sentinel lymph node biopsy in well differentiated thyroid cancer [J]. Journal of Otolaryngology—Head & Neck Surgery, 2013, 42(1):1-5).

Among the above-described dye-based lymph node tracers, isosulfan blue or patent blue has weak binding power to protein, and after being injected, isosulfan blue or patent blue disperses in a small amount of tissues and stains the tissues quickly. However, staining duration of isosulfan blue or patent blue is shorter, so it is necessary to repeatedly inject isosulfan blue or patent blue. Moreover, isosulfan blue and patent blue are expensive and are not produced in China. Staining duration of methylene blue is long, but methylene blue has strong binding power to protein, so it also stains surrounding tissues blue. Nano-carbon has high lymphatic tropism and can accurately position lymph nodes, however, it is not metabolized by the body, its production process is complicated, and its staining speed is low. The nuclide method can accurately position lymph nodes, and is easy to perform in an operation, but a special detection instrument is required, so the cost is high. Moreover, since a radionuclide is used, there is a risk of nuclear pollution.

Therefore, it is important to develop a safe and effective lymphatic tracer for lymphatic tracing in a thyroid carcinoma operation, which effectively positions lymph nodes, predicts whether tumor metastasis occurs, increases the rate of lymph node dissection, and protects the parathyroid glands at the same time, so as to improve the quality of life of the patients with thyroid carcinoma and prolong lifetime of the patients.

SUMMARY

Based on the lymphatic system tropism of mitoxantrone, i.e., mitoxantrone stains lymph nodes near thyroid carcinoma dark blue (the color of mitoxantrone), the present disclosure develops mitoxantrone as a lymphatic tracer for staining lymph nodes near thyroid carcinoma in an operation for a disease related to thyroidectomy, such as thyroid carcinoma, which helps clinical positioning and dissection of lymph nodes and protection of the parathyroid glands.

Therefore, the present disclosure is directed to provide use of mitoxantrone and/or a pharmaceutically acceptable salt thereof in preparation of a lymphatic tracer for preventing parathyroid gland staining in error, preventing parathyroid gland cutting in error or reducing the rate of parathyroid gland cutting in error.

In the present disclosure, unless otherwise specified, the scientific and technical terms used herein have the meanings commonly understood by those skilled in the art. Furthermore, the terms and experimental procedures related to protein and nucleic acid chemistry, molecular biology, cell and tissue culture, microbiology, and immunology that are used herein are all terms and conventional procedures widely used in corresponding fields. Meanwhile, in order to understand the present disclosure better, definitions and descriptions of related terms are provided below.

It is also to be understood that the terms used herein are for the purpose of describing specific embodiments, and are not intended to limit the present disclosure.

As used herein, the terms "patient", "individual", and "subject" are interchangeable, and refer to any single animal that desires treatment, more preferably, a mammal (including, for example, non-human animals, such as cats, dogs, horses, rabbits, zoo animals, cows, pigs, sheep, and non-human primates). In specific embodiments, the patient herein is a human. The patient has, is suspected of having or is at risk of having thyroid tumor. As used herein, the term "disease" refers to any condition that would benefit from treatment, which includes, but is not limited to, chronic and acute diseases or disorders, including those pathological conditions that predispose a mammal to the disease discussed.

As used herein, the term "pharmaceutical preparation" refers to a preparation in a form that allows the biological activity of an active ingredient contained therein to be effective, which does not contain other components that would have unacceptable toxicity to a subject to whom the preparation is administered.

As used herein, the term "pH regulator" refers to a compound or a mixture of multiple compounds for ensuring a pH value of a reconstitution kit to be within an acceptable administration range (a pH value of about 4.0 to 10.5) for humans or mammals. Suitable pH regulators include pharmaceutically acceptable buffers, such as tris(hydroxymethyl)methylglycine (tricine), phosphates, or tris(hydroxymethyl)aminomethane (TRIS); pharmaceutically acceptable acids, such as pharmaceutically acceptable organic acids (e.g., formic acid and acetic acid) or mixtures thereof, or inorganic acids (e.g., hydrochloric acid and phosphoric acid) or mixtures thereof; and pharmaceutically acceptable bases, such as sodium carbonate, sodium bicarbonate, or mixtures thereof. If a used conjugate is in a form of acidic salt, the pH regulator is optionally provided in a separate vial or container, such that a user for the kit may regulate the pH as part of a multi-step procedure.

As used herein, the term "pharmaceutically acceptable excipient" refers to an ingredient rather than an active ingredient in the pharmaceutical preparation that is nontoxic to subjects. Pharmaceutically acceptable excipients include, but are not limited to, buffers, carriers, stabilizers, or preservatives.

As used herein, the term "pharmaceutically acceptable salt" refers to a salt that is not undesirable biologically or in other aspects. Pharmaceutically acceptable salts include acid and base addition salts. The phrase "pharmaceutically acceptable" means that the substance or composition needs to be chemically and/or toxicologically compatible with other ingredients for forming a preparation and/or a mammal to which the preparation is administered.

As used herein, the term "pharmaceutically acceptable acid addition salt" refers to those pharmaceutically acceptable salts formed with inorganic or organic acids, the inorganic acids include, for example, hydrochloric acid, hydrobromic acid, sulfuric acid, nitric acid, carbonic acid, and phosphoric acid, and the organic acids include aliphatic, cycloaliphatic, aromatic, araliphatic, heterocyclic, carboxylic, and sulfonic organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, pamoic acid, phenylacetic acid, methanesulfonic acid (methanesulfonate), ethanesulfonic acid, p-toluenesulfonic acid, and salicylic acid.

The term "pharmaceutically acceptable base addition salt" refers to those pharmaceutically acceptable salts formed with organic or inorganic bases. Examples of the acceptable inorganic base include salts of sodium, potassium, ammonium, calcium, magnesium, iron, zinc, copper, manganese, and aluminum. Salts derived from pharmaceutically acceptable organic nontoxic bases include salts of primary amines, secondary amines, tertiary amines, substituted amines (including naturally occurring substituted amines), and cyclic amines, and salts of basic ion exchange resins, such as salts of isopropylamine, trimethylamine, diethylamine, triethylamine, tripropylamine, ethanolamine, 2-diethylaminoethanol, trimethylamine, dicyclohexylamine, lysine, arginine, histidine, caffeine, procaine, hydrabamine, choline, betaine, ethylenediamine, glucosamine, methylglucamine, theobromine, purine, piperazine, piperidine, N-ethylpiperidine, and polyamine resins.

As used herein, the term "treatment" refers to clinical interventions that attempt to alter the natural course of disease in an individual being treated, and can be used for prophylaxis or in the course of a clinical pathology. Desirable therapeutic effects include, but are not limited to, preventing the occurrence or recurrence of diseases, attenuating symptoms, reducing any direct or indirect pathological consequence of diseases, preventing metastasis, slowing down the progression speed of diseases, relieving or attenuating morbid state, and relieving or improving prognosis.

As used herein, the term "administration" refers to a method for giving a certain dosage of a compound (e.g., a mitoxantrone hydrochloride injection) or a pharmaceutical composition (e.g., a pharmaceutical composition containing an inhibitor or an antagonist) to a subject (e.g., a patient). The compound or the pharmaceutical composition can be administered in any suitable manner, including parenteral administration, intrapulmonary administration, and intranasal administration. If the compound or the pharmaceutical composition is needed for local treatment, it can be intralesionally administered. Parenteral infusion includes, for example, intramuscular administration, intravenous administration, intra-arterial administration, intraperitoneal administration or subcutaneous administration. Drugs can be administered by any suitable routes, for example, by injecting, such as intravenous injecting or subcutaneous injecting, which is partially determined by whether the administration is transient or prolonged. Various administration regimens are contemplated herein, which include, but are not limited to, single administration, multiple administrations at different time points, bolus injecting administration, and pulse infusion.

As used herein, a full analysis set (FAS), a set of subjects according to the principle of intention to treat (ITT) refers to a data set consisting of subjects who participate in a trial, receive treatment, and have baseline therapeutic effect evaluations.

As used herein, a per protocol set (PPS) refers to all subgroups of treated people who have completed a trial and excluded serious protocol violations (referring to objects for study who violate inclusion criteria or exclusion criteria), which is a set of patients who meet inclusion criteria, do not meet exclusion criteria, and have completed therapeutic regimen.

The present disclosure provides a use of mitoxantrone and/or a pharmaceutically acceptable salt thereof in preparation of a lymphatic tracer for preventing parathyroid gland staining in error, preventing parathyroid gland cutting in error or reducing the rate of parathyroid gland cutting in error for a disease related to thyroidectomy.

The present disclosure also provides a method for preventing parathyroid gland staining in error, preventing parathyroid gland cutting in error or reducing the rate of parathyroid gland cutting in error for a disease related to thyroidectomy, which includes administering mitoxantrone and/or a pharmaceutically acceptable salt thereof to a patient.

In a specific embodiment, the disease related to thyroidectomy is selected from thyroid tumor and hyperthyroidism.

In a specific embodiment, the thyroid tumor includes benign thyroid tumor and malignant thyroid tumor.

In a specific embodiment, the benign thyroid tumor is selected from thyroid adenoma or cyst.

In a specific embodiment, the malignant thyroid tumor is selected from thyroid carcinoma and malignant thyroid lymphoma.

In a preferred embodiment, the parathyroid gland cutting in error is parathyroid gland cutting in error in thyroidectomy.

In a preferred embodiment, the thyroidectomy is selected from total thyroidectomy, near total thyroidectomy, lobectomy+isthmectomy for thyroid, partial lobectomy for thyroid, thyroid adenoma enucleation, unilateral total lobectomy for thyroid, and radical thyroidectomy.

In a preferred embodiment, the lymphatic tracer is used for lymphatic tracing in thyroid carcinoma.

In a preferred embodiment, the lymphatic tracer contains mitoxantrone and/or a pharmaceutically acceptable salt thereof and a pharmaceutically acceptable excipient.

In a specific embodiment, the pharmaceutically acceptable excipient includes, but is not limited to, a buffer, a carrier, a stabilizer, and a preservative.

In a specific embodiment, the lymphatic tracer is an injection.

In a specific embodiment, the injection is in a form of solution, lyophilized powder, emulsion, liposome, nanoparticles, nanocrystals, microcrystals, microspheres or gel.

In a specific embodiment, the injection in the form of solution is a sodium chloride injection or a glucose injection.

In a preferred embodiment, the injection is administered subcutaneously or intramuscularly, and preferably, subcutaneously; preferably, the injection is administered locally; preferably, injecting sites are on the thyroid gland and/or tissues and organs around the thyroid; and preferably, 0.2-1.2 mL of injection at a concentration of 5 mg/mL is administered.

In a preferred embodiment, the injection is administered at multiple sites spaced by about 1 cm.

In a preferred embodiment, about 0.1 mL of the injection is administered at each site.

In a preferred embodiment, a total dosage of the injection administered to two sides does not exceed 0.6 mL.

In a preferred embodiment, an operation is performed about 5 min after the administration.

In a specific embodiment, the injection is administered at multiple sites on the thyroid gland, the injecting sites are spaced by about 1 cm according to the size of the thyroid gland, 0.1 mL of the injection is administered at each site, a total dosage of the injection administered to two sides does not exceed 0.6 mL, and an operation is performed about 5 min after the administration.

In a preferred embodiment, the pharmaceutically acceptable salt is a pharmaceutically acceptable salt formed by the mitoxantrone and an inorganic acid or an organic acid.

In a specific embodiment, the inorganic acid is selected from hydrochloric acid, hydrobromic acid, sulfuric acid, nitric acid, carbonic acid, and phosphoric acid.

In a specific embodiment, the organic acid is selected from aliphatic, cycloaliphatic, aromatic, araliphatic, heterocyclic, carboxylic, and sulfonic organic acids, such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, pamoic acid, phenylacetic acid, methanesulfonic acid (methanesulfonate), ethanesulfonic acid, p-toluenesulfonic acid, and salicylic acid.

In a specific embodiment, the pharmaceutically acceptable salt is selected from mitoxantrone hydrochloride, mitoxantrone oxalate, mitoxantrone sulfate, mitoxantrone phosphate, mitoxantrone acetate, and mitoxantrone citrate, and more preferably, the pharmaceutically acceptable salt is mitoxantrone hydrochloride.

In a preferred embodiment, the lymphatic tracer contains a pH regulator.

In a specific embodiment, the pH regulator is one or more selected from the group consisting of hydrochloric acid, phosphoric acid, sulfuric acid, oxalic acid, acetic acid, and citric acid.

In a preferred embodiment, the lymphatic tracer contains an antioxidant.

In a specific embodiment, the antioxidant is one or more selected from the group consisting of sodium sulfite, sodium bisulfite, sodium pyrosulfite, sodium thiosulfate, and disodium edetate; and preferably, sodium pyrosulfite or disodium edetate.

In a specific embodiment, the lymphatic tracer contains mitoxantrone or a salt thereof, sodium chloride, acetic acid, sodium acetate, and sodium pyrosulfite, and more preferably, the lymphatic tracer also contains sodium sulfate.

In a specific embodiment, the lymphatic tracer contains mitoxantrone or a salt thereof, sodium chloride, acetic acid, sodium acetate, and disodium edetate.

In a specific embodiment, a pH value of the injection is in a range of 2.8-4.3.

In a specific embodiment, the content of the mitoxantrone or mitoxantrone in the salt thereof is 1-15 mg/mL, preferably, 2-10 mg/mL, and more preferably, 2 mg/mL, 5 mg/mL or 10 mg/mL, in terms of weight by volume.

In a specific embodiment, the content of the sodium chloride is 3-18 mg/mL, preferably, 4-16 mg/mL, and more preferably, 4 mg/mL, 8 mg/mL or 16 mg/mL, in terms of weight by volume.

In a specific embodiment, the content of the acetic acid is 0.15-1 mg/mL, preferably, 0.23-0.92 mg/mL, and more preferably, 0.23 mg/mL, 0.46 mg/mL or 0.92 mg/mL, in terms of weight by volume.

In a specific embodiment, the content of the sodium acetate is 0.03-0.15 mg/mL, preferably, 0.05-0.1 mg/mL, and more preferably, 0.05 mg/mL or 0.1 mg/mL, in terms of weight by volume.

In a specific embodiment, the content of the antioxidant is 0.05-0.5 mg/mL, preferably, 0.08-0.4 mg/mL, and more preferably, 0.1 mg/mL, 0.2 mg/mL or 0.3 mg/mL, in terms of weight by volume.

In a specific embodiment, the content of the sodium sulfate is 0.05-0.6 mg/mL, preferably, 0.15-0.45 mg/mL, and more preferably, 0.15 mg/mL, 0.3 mg/mL or 0.45 mg/mL, in terms of weight by volume.

In a preferred embodiment, the injection is prepared by the following method:

(1) weighing prescribed amounts of acetic acid, sodium acetate, sodium chloride, and disodium edetate, or weighing prescribed amounts of acetic acid, sodium acetate, sodium chloride, and sodium pyrosulfite, or weighing prescribed amounts of acetic acid, sodium acetate, sodium chloride, sodium pyrosulfite, and sodium sulfate, mixing them with a solvent, and dissolving them to obtain a mixed solution of excipients, preferably, the solvent being water for injecting, preferably, the excipients being dissolved by stirring; and (2) mixing the mixed solution of excipients obtained in the step (1) with prescribed amounts of mitoxantrone and/or a pharmaceutically acceptable salt thereof, preferably, the mitoxantrone and/or the pharmaceutically acceptable salt thereof being dissolved by stirring, preferably, the mitoxantrone and/or the pharmaceutically acceptable salt thereof being dissolved by stirring for 10-30 min.

In a specific embodiment, the method also includes the following step: (3) filtering, preferably, filtering with 0.45 μm and/or 0.22 μm of filter membranes.

In a specific embodiment, the method further includes the following step: (4) bottling and filling with nitrogen gas, preferably, sterilization being performed at 121° C. for 15 min after nitrogen gas is filled.

In a specific embodiment, a pH value of the injection is in a range of 2.8-4.3.

In a preferred embodiment, the injection is prepared by the following method:

(1) weighing prescribed amounts of acetic acid, sodium acetate, sodium chloride, and disodium edetate, or weighing prescribed amounts of acetic acid, sodium acetate, sodium chloride, and sodium pyrosulfite, or weighing prescribed amounts of acetic acid, sodium acetate, sodium chloride, sodium pyrosulfite, and sodium sulfate, adding the excipients into a prescribed amount of water for injecting, and dissolving the excipients by stirring;

(2) adding a prescribed amount of mitoxantrone or a salt thereof after the excipients are dissolved, and dissolving the mitoxantrone or the salt thereof by stirring for 10-30 min;

(3) finely filtering with 0.45 μm and 0.22 μm of filter membranes; and (4) bottling and filling with nitrogen gas, 2 mL each, capping, and sterilizing at 121° C. for 15 min, with a pH value being in a range of 2.8-4.3.

In a specific embodiment, the injection is prepared into a specification of 2 mL:10 mg.

By local administration of the mitoxantrone hydrochloride injection of the present disclosure in an operation for a disease related to thyroidectomy, such as thyroid carcinoma, a lymph node can be well stained and accurately traced, parathyroid gland staining in error is prevented, the rate of parathyroid gland cutting in error can be reduced, and the parathyroid glands are well protected. Moreover, no local or systemic toxic side effect is found after local administration. The mitoxantrone hydrochloride injection of the present disclosure has good tolerance, efficacy, and safety, and provides a new treatment idea in complete eradication of thyroid diseases for patients with diseases related to thyroidectomy (e.g., thyroid carcinoma).

DETAILED DESCRIPTION OF EMBODIMENTS

For purposes of clarity and conciseness of description, features are described herein as part of the same or separate embodiments. However, it is to be understood that the scope of the present disclosure may include some embodiments having combinations of all or some of the described features.

EXAMPLE 1 PREPARATION OF A
MITOXANTRONE HYDROCHLORIDE
INJECTION ACCORDING TO FORMULA 1

| Raw materials and excipients | Usage amount | |
| --- | --- | --- |
| | g | % |
| mitoxantrone hydrochloride | 11.64 | 0.582 |
| sodium chloride | 16.0 | 0.8 |
| acetic acid | 0.92 | 0.046 |
| sodium acetate | 0.10 | 0.005 |
| disodium edetate | 0.40 | 0.02 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.5.

EXAMPLE 2 PREPARATION OF A MITOXANTRONE HYDROCHLORIDE INJECTION ACCORDING TO FORMULA 2

| Raw materials and excipients | Usage amount | |
|---|---|---|
| | g | % |
| mitoxantrone hydrochloride | 23.28 | 1.164 |
| sodium chloride | 32.0 | 1.6 |
| acetic acid | 1.84 | 0.092 |
| sodium acetate | 0.20 | 0.01 |
| sodium pyrosulfite | 0.40 | 0.02 |
| sodium sulfate | 0.60 | 0.03 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.4.

EXAMPLE 3 PREPARATION OF A MITOXANTRONE HYDROCHLORIDE INJECTION ACCORDING TO FORMULA 3

| Raw materials and excipients | Usage amount | |
|---|---|---|
| | g | % |
| mitoxantrone hydrochloride | 2.91 | 0.1455 |
| sodium chloride | 16.0 | 0.8 |
| acetic acid | 0.92 | 0.046 |
| sodium acetate | 0.10 | 0.005 |
| disodium edetate | 0.40 | 0.02 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.6.

EXAMPLE 4 PREPARATION OF A MITOXANTRONE HYDROCHLORIDE INJECTION ACCORDING TO FORMULA 4

| Raw materials and excipients | Usage amount | |
|---|---|---|
| | g | % |
| mitoxantrone hydrochloride | 11.64 | 0.582 |
| sodium chloride | 16.0 | 0.8 |
| acetic acid | 0.92 | 0.046 |
| sodium acetate | 0.10 | 0.005 |
| sodium pyrosulfite | 0.20 | 0.01 |
| sodium sulfate | 0.30 | 0.015 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.7.

EXAMPLE 5 PREPARATION OF A MITOXANTRONE HYDROCHLORIDE INJECTION ACCORDING TO FORMULA 5

| Raw materials and excipients | Usage amount | |
|---|---|---|
| | g | % |
| mitoxantrone hydrochloride | 23.28 | 1.164 |
| sodium chloride | 16.0 | 0.8 |
| acetic acid | 0.92 | 0.046 |
| sodium acetate | 0.10 | 0.005 |
| sodium pyrosulfite | 0.40 | 0.020 |
| sodium sulfate | 0.90 | 0.045 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.6.

EXAMPLE 6 PREPARATION OF A MITOXANTRONE HYDROCHLORIDE INJECTION ACCORDING TO FORMULA 6

| Raw materials and excipients | Usage amount | |
| --- | --- | --- |
| | g | % |
| mitoxantrone hydrochloride | 23.28 | 1.164 |
| sodium chloride | 16.0 | 0.8 |
| acetic acid | 0.92 | 0.046 |
| sodium acetate | 0.10 | 0.005 |
| disodium edetate | 0.60 | 0.03 |
| water for injecting (made up to) | 2,000 mL | — |

Prescribed amounts of sodium chloride, acetic acid, sodium acetate, and disodium edetate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.7.

EXAMPLE 7 PREPARATION OF A MITOXANTRONE HYDROCHLORIDE INJECTION ACCORDING TO FORMULA 7

| Raw materials and excipients | Usage amount | |
| --- | --- | --- |
| | g | % |
| mitoxantrone hydrochloride | 11.64 | 0.582 |
| sodium chloride | 8.0 | 0.4 |
| acetic acid | 0.46 | 0.023 |
| sodium acetate | 0.10 | 0.005 |
| sodium pyrosulfite | 0.40 | 0.020 |
| water for injecting (made up to) | 2,000 mL | — |

Prescribed amounts of sodium chloride, acetic acid, sodium acetate, and sodium pyrosulfite were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.9.

EXAMPLE 8 PREPARATION OF A MITOXANTRONE HYDROCHLORIDE INJECTION ACCORDING TO FORMULA 8

| Raw materials and excipients | Usage amount | |
| --- | --- | --- |
| | g | % |
| mitoxantrone hydrochloride | 5.82 | 0.291 |
| sodium chloride | 8.0 | 0.4 |

-continued

| Raw materials and excipients | Usage amount | |
| --- | --- | --- |
| | g | % |
| acetic acid | 0.46 | 0.023 |
| sodium acetate | 0.10 | 0.005 |
| sodium pyrosulfite | 0.40 | 0.020 |
| sodium sulfate | 0.60 | 0.03 |
| water for injecting (made up to) | 2,000 mL | — |

Prescribed amounts of sodium chloride, acetic acid, sodium acetate, sodium pyrosulfite, and sodium sulfate were weighed, added into a prescribed amount of water for injecting, and dissolved by stirring; a prescribed amount of mitoxantrone hydrochloride was added after the excipients were dissolved, and dissolved by stirring for 30 min; and the mixed solution was finely filtered with 0.45 μm and 0.22 μm of filter membranes, bottled and filled with nitrogen gas, capped, and sterilized at 121° C. for 15 min. A pH value of the mitoxantrone hydrochloride injection was detected to be 3.5.

EXAMPLE 9 STUDIES ON PHARMACOKINETIC AND PHARMACODYNAMIC OF A MITOXANTRONE HYDROCHLORIDE INJECTION

A target organ of a mitoxantrone hydrochloride injection for lymphatic tracing is a lymph node in the thyroid drainage area. When mitoxantrone hydrochloride is compounded with hydrochloric acid, a uniform acidic solution can be formed. After a mitoxantrone hydrochloride injection is administered to the tissue space, the pH of the microenvironment changes, and mitoxantrone hydrochloride will gradually precipitate into nanocrystals. The crystals prevent mitoxantrone hydrochloride from entering the blood circulation through capillaries. Due to high permeability of lymphatic capillaries, mitoxantrone hydrochloride can enter the lymphatic capillaries through endothelial cell space as well as pinocytosis and phagocytosis of endothelial cells, reach regional lymph nodes through lymphatic drainage and enrich in regional lymph nodes, and stay in the lymph nodes for a period of time, thereby achieving effects of staining and tracing of the lymph nodes.

In order to test the safety and efficacy of a mitoxantrone hydrochloride injection for lymphatic tracing in tracing of lesion-draining lymph nodes in a patient with thyroid carcinoma, and to test the tolerance and in vivo pharmacokinetics of the mitoxantrone hydrochloride injection for lymphatic tracing in the subject with thyroid carcinoma, so as to determine a safe dose range, this example adopted a single-center, randomized, open, and blank-controlled trial design. After the thyroid was fully exposed, a mitoxantrone hydrochloride injection for lymphatic tracing was administered at multiple sites on the thyroid gland. According to the size of the thyroid, a total dose of the injection did not exceed 0.6 mL. The tolerance in human being and pharmacokinetics in subjects were tested group by group, and the efficacy of the investigational drug was observed at the same time.

Pharmacokinetic results: the mitoxantrone hydrochloride injection is rapidly absorbed after being peritumorally administered, and the peak is basically reached 10 min after injecting. Moreover, the drug is metabolized rapidly after entering the blood, and the drug in the plasma is almost completely metabolized 30 min after the administration. In addition, the plasma concentration after the administration generally shows a dose-dependent trend, plasma concentrations in different subjects in a low-dose group are all lower than the lower limit of quantification at various time points; plasma concentrations in various patients in medium- and high-dose groups are equal to and higher than the lower limit of quantification at 3 time points at most; and the detected maximum concentration is 13.10 ng/mL only. In the prior art document (Zhu Jianming et al., "Cutting in error of Parathyroid Glands in Thyroid Operation and Postoperative Hypocalcemia", Chinese Journal of Modern Operative Surgery, April 2010, Volume 14, Issue 2, p. 112-114), high-dose mitoxantrone is used for chemotherapeutically treating ovarian cancer. The maximum tolerated total dosage of mitoxantrone administered by intravenous bolus injecting is 75 mg/m$^2$, and AUC at this dose is 560-1700 ng·h/mL, which is 135.4-411.0 times the maximum AUC (248.15 ng·min/ml) in the present trial. It can be seen that the mitoxantrone hydrochloride injection does not cause toxic side effects after being peritumorally administered, and there is no security risk after local administration.

Pharmacodynamic results: after the tracer is injected into the subject, the stained lymph nodes do not fade until the lymph node dissection is completed. Therefore, the success rate of sustained tracing is 100%.

EXAMPLE 10 APPLICATION OF A MITOXANTRONE HYDROCHLORIDE INJECTION FOR LYMPHATIC TRACING IN AN OPERATION FOR A PATIENT WITH THYROID CARCINOMA

1. Clinical Trial Design

The present example adopted a multi-center and randomized clinical trial design. Subjects meeting scheme requirements were randomly grouped in a ratio of 1:1 for comparison of the efficacy and safety of the mitoxantrone hydrochloride injection for lymphatic tracing in treatment for patients with thyroid carcinoma. The scheme requirements were specifically as follows:

Aged 18-70 (including 18 and 70), no gender preference

Preoperative clinical diagnosis of thyroid carcinoma, planning to undergo a radical operation for thyroid carcinoma Planning to undergo total thyroidectomy and total central lymph node dissection according to preoperative evaluation No obvious operative contraindications in routine preoperative examination Able to well communicate with researchers and complete the study in accordance with study regulations Voluntarily participating in the study and sign informed consent An experiment group (each patient was administered with the mitoxantrone hydrochloride injection in which the content of an active ingredient was 5 mg/mL at multiple sites on the thyroid gland, the injecting sites were spaced by about 1 cm according to the size of the thyroid, about 0.1 mL of the injection was administered at each site, a total dosage of the injection administered to two sides did not exceed 0.6 mL, and an operation was performed about 5 min after the administration) and a control group (each patient underwent a conventional operation without administration of the mitoxantrone hydrochloride injection) were checked, and the number of parathyroid glands cut in error, the total number of dissected lymph nodes, and the number of metastatic lymph nodes were recorded.

Safety Evaluation Indicators

Safety evaluations were conducted throughout the study. Subjects with early withdrawal underwent the safety evaluation before withdrawal. The safety evaluation included changes in vital signs, physical examination, electrocardiogram, clinical laboratory test indicators (blood routine, urine routine, blood biochemistry, coagulation function, pregnancy test, etc.), adverse events and serious adverse events, and early withdrawal due to safety or tolerance.

2. Efficacy Results of the Clinical Trial

Results of the clinical trial show that the rate of parathyroid gland cutting in error in the conventional operations is about 27%, the rate of parathyroid gland cutting in error in the operations using the product of the present disclosure is 7% or less, and the rate of parathyroid gland cutting in error and the number of parathyroid glands cut in error in the individuals undergoing the operations using the product of the present disclosure are both less than those in the individuals undergoing the conventional operations. In this study, for the evaluation of the main therapeutic effect indicators, statistical analysis is performed by means of a PPS data set and an FAS data set, respectively, and the conclusions are consistent. Furthermore, sensitivity analysis results are also consistent. There is a significant difference (P<0.001) between the experiment group and the control group in the main therapeutic effect indicators, and no obvious adverse effects are found.

3. Safety Evaluation Results of the Clinical Trial

Phase I clinical trial shows that the mitoxantrone hydrochloride injection for lymphatic tracing enters the blood circulation in a very small amount after being administered locally, does not cause systemic toxic side effects, and has good safety. Phase II and Phase III clinical trials show that when the mitoxantrone hydrochloride injection for lymphatic tracing is used for lymphatic tracing in the operations for the patients with thyroid carcinoma in the experiment group and the blank control group, the percentage of adverse events (AE), the percentage of serious adverse events (SAE), and the percentage of AE of grade 3 or more in the subjects are all similar, and no AE and SAE related to the investigational drug occur. A chi-square test is used for comparison of the groups, and there is no statistically significant difference between the two groups in occurrence rates of AE, SAE, and AE of grade 3 or more. Therefore, it can be concluded that the safety results of the experimental group are similar to those of the blank control group, and are good.

The results of the above clinical trials show that:

(1) the mitoxantrone hydrochloride injection can well protect the parathyroid glands;

(2) the mitoxantrone hydrochloride injection can well stain lymph nodes and can accurately trace the lymph nodes;

(3) the investigational drug does not stain the parathyroid glands in error;

(4) the investigational drug can dissect more lymph nodes while applied in a thyroid operation;

(5) the lymph nodes with a size of ≤2 mm, >2 mm and ≤5 mm, and >5 mm and ≤10 mm are detected and dissected, wherein there is a significant difference between the experimental group and the control group, and there is no statistically significant difference between the experimental group and the control group in the lymph nodes with a size of >10 mm; and (6) after the investigational drug is administered locally, no local or systemic toxic side effect is found, and no adverse event or adverse effect related to the investigational drug occurs, indicating that the investigational drug has good tolerance and safety.

It can be known from the above results that the study of these clinical trials has good efficacy and safety. By using the mitoxantrone hydrochloride injection for tracing to position and dissect lymph nodes on the basis of its staining function for lymph nodes, lymph nodes can be accurately traced, and more lymph nodes can be dissected, thereby preventing parathyroid gland cutting in error, reducing the rate of parathyroid gland cutting in error, and providing a new treatment idea in complete eradication of thyroid carcinoma for patients with thyroid carcinoma.

EXAMPLE 11 APPLICATION OF A MITOXANTRONE HYDROCHLORIDE INJECTION FOR LYMPHATIC TRACING IN A RADICAL OPERATION FOR A PATIENT WITH THYROID CARCINOMA

Preoperative diagnosis: thyroid carcinoma

Postoperative diagnosis: thyroid carcinoma

Operation name: a radical operation for thyroid carcinoma (bilateral total lobectomy for thyroid+bilateral VI- and VII-level lymph node dissection)

Anesthesia method: general anesthesia

Operative procedures are as follows. The patient was checked. After the patient was anesthetized successfully, the patient's shoulders were supported by a pillow, the neck was tilted back, and the conventional surgical field was disinfected with iodine complex and draped. An arc-shaped incision with a length of about 7 cm was formed below the neck and anastomosed with the dermatoglyph, the skin, the subcutaneous tissue, and the platysma to the anterior cervical fascia were cut open layer by layer, and flaps were dissociated upwards and downwards along the space between the platysma and the anterior cervical fascia: the anterior cervical fascia was cut open at the midline of the neck, and the anterior cervical muscles were dissociated to both sides to reach the surface of the thyroid. It was found by exploration that the thyroid was softer in texture, with multiple tough nodules in two lobes, of which the right lobe was accessible with a hard nodules having a size of about 1 cm. 0.1 mL of the mitoxantrone hydrochloride injection for lymphatic tracing was administered under the thyroid capsule at upper and lower portions, spaced by 1 cm, of the left thyroid lobe as well as upper and lower portions, spaced by 1 cm, of the right thyroid lobe, respectively (total 0.4 mL), and the drug was withdrawn. After the puncture sites were pressed for 5 min, the thyroid and lymph nodes were gradually stained blue. First, right lobectomy was performed, the lateral of the right thyroid lobe was dissociated, the middle thyroid veins in the right lobe were severed, and anterior laryngeal lymph nodes and the thyroid conical lobe were cut and removed. The isthmus close to the right lobe was dissociated, the right thyroid lobe was pulled to the left, and upper and lower polar vessels in the right thyroid lobe were severed. The thyroid gland was pulled upwards, and the recurrent laryngeal nerve was carefully separated from the dorsal part of the thyroid and protected carefully: the right thyroid lobe was dissociated from the inside out to completely cut and remove the right thyroid lobe. Left lobectomy was performed in a similar way. The bilateral recurrent laryngeal nerves were dissociated throughout the lobectomy, VI- and VII-level regional lymphatic adipose tissues (up to the level of the hyoid bone, from the external carotid artery to the medial border, down to the superior border of the innominate artery) were dissected under the guidance of the lymphatic tracer, and visible parathyroid glands were reserved in situ throughout the lobectomy. The bleeding in the wound was carefully stopped; after no obvious active bleeding was observed, the numbers of gauzes and instruments were checked; and after confirmation, the layers from the anterior cervical fascia to the subcutaneous tissue were closed layer by layer by using absorbable sutures to suture the wound. The operation was performed smoothly, with little bleeding, and no blood transfusion was required. After the operation, the tracheal intubation was successfully removed, and the patient returned to the ward safely without hoarseness. The removed tissues were examined pathologically.

Pathological examination results: metastatic carcinoma of lymph nodes (the right paratracheal area: 0/0; the pretracheal area: 1/1; the left paratracheal area: 1/6; and the prelaryngeal area: 0/0), with a small amount of visible thyroid tissues (the right paratracheal area and the prelaryngeal area).

No parathyroid gland is cut in error, and a total of 7 lymph nodes are detected, which include 2 lymph nodes with a size of ≤2 mm, 5 lymph nodes with a size of >2 mm and ≤5 mm, and 0 lymph node with a size of >5 mm and ≤10 mm. The above detected lymph nodes are all stained with the staining rate of 100%.

The invention claimed is:

1. A lymphatic tracer for preventing parathyroid gland staining in error, preventing parathyroid gland cutting in error or reducing the rate of parathyroid gland cutting in error for a disease related to thyroidectomy, wherein the lymphatic tracer contains mitoxantrone hydrochloride, sodium chloride, acetic acid, sodium acetate and antioxidant;

the antioxidant is sodium pyrosulfite or disodium edetate;

the content of the mitoxantrone hydrochloride is 1-15 mg/mL;

the content of the sodium chloride is 3-18 mg/mL;

the content of the acetic acid is 0.15-1 mg/mL;

the content of the sodium acetate is 0.03-0.15 mg/mL;

the content of the antioxidant is 0.05-0.5 mg/mL; and the lymphatic tracer is an injection.

2. A method for preventing parathyroid gland staining in error, preventing parathyroid gland cutting in error or reducing the rate of parathyroid gland cutting in error for a disease related to thyroidectomy, comprising:

administering the lymphatic tracer according to claim 1 to a patient, wherein the lymphatic tracer is an injection;

the injection is administered at multiple sites spaced by about 1 cm;

injecting sites are on thyroid glands and/or tissues and organs around the thyroid; and 0.2-1.2 mL of the injection at a concentration of 5 mg/mL is administered.

3. The method according to claim 2, wherein the parathyroid gland cutting in error is parathyroid gland cutting in error in thyroidectomy.

4. The method according to claim 3, wherein the thyroidectomy is selected from total thyroidectomy, near total thyroidectomy, lobectomy+isthmectomy for thyroid, partial lobectomy for thyroid, thyroid adenoma enucleation, unilateral total lobectomy for thyroid, and radical thyroidectomy; and the lymphatic tracer is used for lymphatic tracing in thyroid carcinoma.

5. The method according to claim 2, wherein the injection is administered subcutaneously or intramuscularly;

the injection is administered locally;

about 0.1 mL of the injection is administered at each site;

a total dosage of the injection administered to two sides does not exceed 0.6 mL; and an operation is performed about 5 min after the administration for the injection.

6. Method for preparing the lymphatic tracer described in claim 1, comprising the following steps:

(1) weighing prescribed amounts of acetic acid, sodium acetate, sodium chloride, and disodium edetate, or weighing prescribed amounts of acetic acid, sodium acetate, sodium chloride, and sodium pyrosulfite, or weighing prescribed amounts of acetic acid, sodium acetate, sodium chloride, sodium pyrosulfite, and sodium sulfate, mixing them with a solvent, and dissolving them to obtain a mixed solution of excipients; and (2) mixing the mixed solution of excipients obtained in the step (1) with prescribed amounts of mitoxantrone hydrochloride;

(3) filtering;

(4) bottling and filling with nitrogen gas.

7. The method according to claim 6, wherein the solvent in step (1) is water for injecting;

the dissolving in step (1) is dissolving excipients by stirring;

the mixing in step (2) is dissolving the mitoxantrone hydrochloride by stirring;

the filtering in step (3) is filtering with 0.45 μm and/or 0.22 μm of filter membrane;

sterilization being performed at 121° C. for 15 min after filling with nitrogen gas;

a pH value of the injection is in a range of 2.8-4.3; and the injection is prepared into a specification of 2 mL:10 mg.

8. The lymphatic tracer according to claim 1, wherein the antioxidant is sodium pyrosulfite the lymphatic tracer further contains sodium sulfate; and the content of the sodium sulfate is 0.05-0.6 mg/mL, in terms of weight by volume.

9. The lymphatic tracer according to claim 8, wherein the content of the sodium sulfate is 0.15-0.45 mg/mL, in terms of weight by volume.

10. The lymphatic tracer according to claim 1, wherein a pH value of the injection is in a range of 2.8-4.3;

the content of the mitoxantrone hydrochloride is 2-10 mg/mL, in terms of weight by volume;

the content of the sodium chloride is 4-16 mg/mL, in terms of weight by volume;

the content of the acetic acid is 0.23-0.92 mg/mL, in terms of weight by volume;

the content of the sodium acetate is 0.05-0.1 mg/mL, in terms of weight by volume; and the content of the antioxidant is 0.08-0.4 mg/mL, in terms of weight by volume.

11. The lymphatic tracer according to claim 10, wherein the content of the mitoxantrone hydrochloride is 2 mg/mL, 5 mg/mL or 10 mg/mL, in terms of weight by volume;

the content of the sodium chloride is 4 mg/mL, 8 mg/mL or 16 mg/mL, in terms of weight by volume;

the content of the acetic acid is 0.23 mg/mL, 0.46 mg/mL or 0.92 mg/mL, in terms of weight by volume;

the content of the sodium acetate is 0.05 mg/mL or 0.1 mg/mL, in terms of weight by volume; and the content of the antioxidant is 0.1 mg/mL, 0.2 mg/mL or 0.3 mg/mL, in terms of weight by volume.

12. The method according to claim 2, wherein the disease related to thyroidectomy selected from thyroid tumor or hyperthyroidism.

13. The method according to claim 12, wherein the thyroid tumor is benign thyroid tumor or malignant thyroid tumor.

14. The method according to claim 13, wherein the benign thyroid tumor being selected from thyroid adenoma or cyst; and the malignant thyroid tumor being selected from thyroid carcinoma or malignant thyroid lymphoma.

15. The method according to claim 5, wherein the injection is administered subcutaneously.

* * * * *